United States Patent
Anderskewitz et al.

(10) Patent No.: US 6,576,669 B2
(45) Date of Patent: Jun. 10, 2003

(54) USE OF AN LTB4 ANTAGONIST FOR THE TREATMENT OR PREVENTION OF DISEASES CAUSED BY INCREASED EXPRESSION OF MUCIN GENES

(75) Inventors: Ralf Anderskewitz, Laupheim (DE); Christopher J. Montague Meade, Bingen (DE); Franz Birke, Ingelheim (DE); Hans Michael Jennewein, Wiesbaden (DE); Birgit Jung, Schwabenheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/050,409

(22) Filed: Jan. 16, 2002

(65) Prior Publication Data

US 2002/0137792 A1 Sep. 26, 2002

Related U.S. Application Data

(60) Provisional application No. 60/266,833, filed on Feb. 6, 2001.

(30) Foreign Application Priority Data

Jan. 16, 2001 (GB) .............................................. 0101128

(51) Int. Cl.$^7$ ............................................ A61K 31/155
(52) U.S. Cl. ....................................... 514/637; 514/851
(58) Field of Search ................................. 514/637, 851

(56) References Cited

U.S. PATENT DOCUMENTS

| | | | |
|---|---|---|---|
| 5,686,496 A | * 11/1997 | Anderskewitz et al. | ..... 514/637 |
| 5,723,492 A | 3/1998 | Chandrakumar et al. | |
| 5,731,332 A | 3/1998 | Anderskewitz et al. | |
| 6,127,423 A | * 10/2000 | Anderskewitz et al. | ..... 514/637 |
| 6,417,382 B2 | * 7/2002 | Brandenburg et al. | ........ 558/44 |

FOREIGN PATENT DOCUMENTS

WO 9602497 A1 * 2/1996

OTHER PUBLICATIONS

Birke et al., "In Vitro and in Vivo Pharmacological Characterization of BIIL 284, a Novel and Potent Leukotriene B4 Receptor Antagonist", Journal of Pharmacology and Experimental Therapeutics (2001), 297(1), pp. 458–466.*

Li JD, Dohrman AF, Gallup M, et al.; Transcriptional activation of mucin by *Pseudomonas aeruginosa* lipopolysaccharide in the pathogenesis of cystic fibrosis lung disease. Proc. Natl. Acad. Sci., 1997, 967–972, 94; USA.

Dohrman A, Miyata S, Gallup M, et al.; Mucin gene (MUC 2 and MUC 5AC) upregulation by Gram–positive and Gram–negative bacteria. Biochim. Biophys. Acta., 1998, 251–259, 1406; FR.

Konstan MW, Walenga RW, Hilliard KA, Hilliard JB; Leukotriene B4 markedly elevated in the epithelial lining fluid of patients with cystic fibrosis. Am. Rev. Respir. Dis., 1993, 896–901, 148; USA.

Zakrzewski JT, Barnes NC, Piper PJ, Costello JF; Detection of sputum eicosanoids in cystic fibrosis and in normal saliva by bioassay and radioimmunoassay. Br. J. Clin. Pharmacol., 1987, 19–27, 23; UK.

Takeyama K, Agusti C, Ueki I, Lausier J, Cardell LO, Nadel JA; Neutrophil–dependent goblet cell degranulation: role of membrane–bound elastase and adhesion molecules. Am. J. Physiol., 1998, L294–L302, 275; USA.

Takeyama K, Dabbagh K, Lee HM, et al.; Epidermal growth factor system regulates mucin production in airways. Proc. Natl. Acad. Sci., 1999; 3081–3086, 96; USA.

Klinger JD, Tandler B, Liedtke CM, Boat TF; Proteinases of *Pseudomonas aeruginosa* evoke mucin release by tracheal epithelium. J. Clin. Invest, 1984, 1669–1678, 74; USA.

Ichikawa JK, Norris A, Bangera MG, et al., Interaction of *Pseudomonas aeruginosa* with epithelial cells: identification of differentially regulated genes by expression microassay analysis of human cDNAs. Proc. Natl. Acad. Sci., 2000, 9659–9664, 97; USA.

Doring G, et al.; "Antibiotic therapy against *Pseudomonas aeruginosa* in cystic fibrosis: a European consensus." Eur. Respir. J., 2000, 749–767, 16; UK.

Houtmeyers E, et al.; Effects of drugs on mucus clearance. Eur. Respir. J., 1999, 452–467, 14; UK.

Bedrossian CW, Greenberg SD, Singer DB, Hansen JJ, Rosenberg HS; The lung in cystic fibrosis. A quantitative study including prevelence of pathologic findings among different age groups. Hum Pathol, 1976, 195–204, 7; USA.

Cheung AT, Moss RB, Kurland G, Leong AB, Novick WJ Jr.,; Chronic *Pseudomonas aeruginosa* endobronchitis in rhesus monkeys: II A histopathologic analysis. J. Med Primatol.; 1993, 257–262, 22; USA.

* cited by examiner

Primary Examiner—Kevin E. Weddington
(74) Attorney, Agent, or Firm—T. X. Witkowski; R. P. Raymond

(57) ABSTRACT

Medicaments and pharmaceutical kits comprising an $LTB_4$ antagonist of formula (I)

(I)

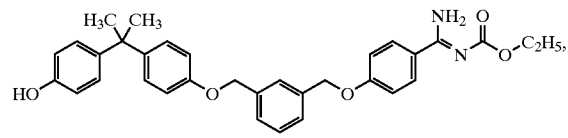

a tautomer thereof or a pharmaceutically acceptable salt thereof, and methods of treating or preventing cystic fibrosis, diseases caused by increased expression of mucin genes in the bronchial or gastrointestinal epithelium, or hyperplasia of goblet cells induced by toxins of products of pathogenic bacteria in a patient in need of such treatment, the method comprising administering to the patient a therapeutically effective amount of an $LTB_4$ antagonist of formula (I).

8 Claims, No Drawings

USE OF AN LTB4 ANTAGONIST FOR THE TREATMENT OR PREVENTION OF DISEASES CAUSED BY INCREASED EXPRESSION OF MUCIN GENES

RELATED APPLICATIONS

Benefit under 35 U.S.C. §119(e) of prior provisional application Ser. No. 60/266,833, filed Feb. 6, 2001, is hereby claimed.

FIELD OF THE INVENTION

The invention relates to the use of a $LTB_4$ antagonist or a pharmaceutically acceptable salt thereof for the preparation of a medicament for the treatment and/or prevention of diseases caused by increased expression of mucin genes in the bronchial or gastrointestinal epithelium.

BACKGROUND OF THE INVENTION

Cystic fibrosis (CF) is an inherited disease primarily due to a defect in the cystic fibrosis trans-membrane regulating protein (CFTR). This results in abnormal chloride transfer across epithelial membranes. Symptoms appear in a number of organ systems, but for most patients the most important pathological changes associated with the CFTR defect are those in the lung. Patients with cystic fibrosis produce excessive quantities of viscous mucus which readily becomes infected. Recurring infections are associated with worsening of the condition of the patient and an increased high risk of death. Exactly how the CFTR defect causes increased mucus production is not known. One hypothesis is that the CFTR mutation causes changes in the tracheal epithelium which engender chronic bacterial infection, particularly with *Pseudomonas aeruginosa*. These bacteria stimulate expression of mucin genes, such as MUC-2 and MUC-5. Overproduction of mucus, combined with mucus dehydration related to the underlying chloride channel defect, lead to formation of mucus plugs and eventually to lung failure (J. D. Li, A. F. Dohrman, M. Gallup et al., *Transcriptional Activation of Mucin by Pseudomonas aeruginosa Lipopolysaccharide in the Pathogenesis of Cystic Fibrosis Lung Disease*, Proc. Natl. Acad. Sci. U.S.A., 1997, 94:967–972; A. Dohrman, S. Miyata, M. Gallup et al., *Mucin Gene (MUC 2 and MUC 5AC) Upregulation by Gram-positive and Gram-Negative Bacteria*, Biochim. Biophys. Acta, 1998, 1406:251–259).

Cystic fibrosis is associated with markedly elevated levels of leukotriene $B_4$ in the epithelial lining fluid of the lung (M. W. Konstan, R. W. Walenga, K. A. Hilliard, J. B. Hilliard, *Leukotriene B4 Markedly Elevated in the Epithelial Lining Fluid of Patients with Cystic Fibrosis*, Am. Rev. Respir. Dis., 1993, 148:896–901), and this elevation is also detectable in the sputum (J. T. Zakrzewski, N. C. Barnes, P. J. Piper, J. F. Costello, *Detection of Sputum Eicosanoids in Cystic Fibrosis and in Normal Saliva by Bioassay and Radioimmunoassay*, Br. J. Clin. Pharmacol., 1987, 23:19–27). The source of this $LTB_4$ is unclear since both inflammatory cells such as neutrophils which are much more abundant in the CF lung as well as epithelial cells have the necessary enzyme machinery to synthesize this leukotriene.

Similarly, the exact mechanism by which *Pseudomonas aeruginosa* stimulates the increased expression of mucin genes in the bronchial epithelium is also unclear. Certainly, both clinically and experimentally, infection with *Pseudomonas aeruginosa* is associated with neutrophil infiltration into the lung, and products of activated neutrophils such as elastase, TGFbeta and TNFalpha are known to be able to increase the amount of mucin specific RNA in the bronchial epithelium either by stimulating the transcription of the genes or by impeding RNA degradation (K. Takeyama, C. Agusti, I. Ueki, J. Lausier, L. O. Cardell, J. A. Nadel, *Neutrophil-Dependent Goblet Cell Degranulation: Role of Membrane-Bound Elastase and Adhesion Molecules*, Am. J. Physiol. 1998, 275:L294–L302; K. Takeyama, K. Dabbagh, H. M. Lee et al., *Epidermal Growth Factor System Regulates Mucin Production in Airways*, Proc. Natl. Acad. Sci. U.S.A., 1999, 96:3081–3086). However, there are also direct effects of *Pseudomonas aeruginosa* on pulmonary epithelial cells, via bacterial lipopolysaccharides (J. D. Li, A. F. Dohrman, M. Gallup et al., 1997; loc. cit.), via bacterial proteases (J. D. Klinger, B. Tandler, C. M. Liedtke, T. F. Boat, *Proteinases of Pseudomonas aeruginosa Evoke Mucin Release by Tracheal Epithelium*, J. Clin. Invest., 1984, 74:1669–1678), or via bacterial adhesins (J. K. Ichikawa, A. Norris, M. G. Bangera et al., *Interaction of Pseudomonas aeruginosa with Epithelial Cells: Identification of Differentially Regulated Genes by Expression Microarray Analysis of Human cDNAs*, Proc. Natl. Acad. Sci. U.S.A., 2000; 97:9659–9664). The role of $LTB_4$ in both the neutrophil-mediated and the direct effects of *Pseudomonas aeruginosa* on the pulmonary epithelium is unknown.

SUMMARY OF THE INVENTION

The present invention relates to the use of an $LTB_4$ antagonist of formula (I), a tautomer thereof or a pharmaceutically acceptable salt thereof for the preparation of a medicament for the treatment and/or prevention of diseases caused by increased expression of mucin genes in the bronchial or gastrointestinal epithelium, in particular diseases caused by *Pseudomonas aeruginosa* such as cystic fibrosis.

Another aspect of the invention is a method for the treatment of patients suffering from diseases caused by increased expression of mucin genes in the bronchial or gastrointestinal epithelium which method comprises administering to the patient in need thereof an effective amount of a compound of formula (I), a tautomer thereof or a pharmaceutically acceptable salt thereof.

The invention further provides a medicament containing, separately or together, (A) a compound of formula (I), a tautomer thereof or a pharmaceutically acceptable salt thereof;

(B) one or more additional active ingredients selected from the group consisting of antibiotics, $LTA_4$ hydrolase inhibitors, 5-lipoxygenase inhibitors and agents that enhance mucus clearance; and (C) optionally a pharmaceutically acceptable carrier, for simultaneous, sequential or separate administration in the treatment of diseases caused by increased expression of mucin genes in the bronchial or gastrointestinal epithelium.

Furthermore, the invention relates to a pharmaceutical kit comprising at least two separate unit dosage forms (A) and (B):

(A) one of which comprises a composition containing a compound of formula (I), a tautomer thereof or a pharmaceutically acceptable salt thereof and optionally a pharmaceutically acceptable carrier;

(B) one of which comprises a composition containing one or more additional active ingredients selected from the group consisting of antibiotics, $LTA_4$ hydrolase inhibitors, 5-lipoxygenase inhibitors and agents that enhance mucus clearance and optionally a pharmaceutically acceptable carrier.

DETAILED DESCRIPTION OF THE INVENTION

The pharmaceutically acceptable salts of the compound of formula (I) include, for example salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o- or p-hydroxybenzoic, p-chlorobenzoic, methanesulfonic, p-toluenesulfonic, and 3-hydroxy-2-naphthalene carboxylic acids. Most preferred is the compound of formula (I) as such, i.e., in form of the free base.

In a preferred embodiment of the present invention the compound of formula I is used for the preparation of a medicament for the prevention of goblet cell hyperplasia induced by products of pathogen bacteria, in particular products derived from *Pseudomonas aeruginosa*.

In addition, to being useful to inhibit *Pseudomonas aeruginosa*-induced mucus production in cystic fibrosis patients, the compound of formula (I) will also be useful, either alone or in combination with other therapeutic agents such as antibiotics, for the treatment of mucus hypersecretion associated with *Pseudomonas aeruginosa* infection in patients without a defect in the CFTR gene.

The compound of formula (I) will further be useful for the treatment of mucoid enterocolitis, such as associated with infection with *Pseudomonas aeruginosa*, as well as mucoid enterocolitis associated with other pathogens such as Shigella. Particularly useful will be the application of the compound of formula (I) in combination with antibacterial therapy.

The compound of formula (I) can be used in the therapy of cystic fibrosis either alone or in combination with other therapies (B). It has now surprisingly been found that a significant unexpected therapeutic benefit, particularly a synergistic therapeutic benefit, in the treatment of diseases caused by increased expression of mucin genes in the bronchial or gastrointestinal epithelium can be achieved by combination therapy using the compound of formula (I) and an active ingredient (B).

For instance, it is possible using this combination therapy to reduce the dosages required for a given therapeutic effect considerably compared with those required using treatment with (B) alone, thereby minimizing possibly undesirable side effects.

Furthermore, this combination therapy exhibits both a fast onset of action and a long duration of action, so that patients feel a rapid improvement in their condition and a reduced need for short-acting rescue medicaments.

Particularly useful may be combination of the compound of formula (I) with antibiotic or antibacterial therapies (B1) for the bacterial airway superinfection. These therapies will include, but not be confined to those antibiotics listed with appropriate dosages in Table 1 of the published consensus statement of G. Döring et al., Antibiotic Therapy Against *Pseudomonas aeruginosa* in Cystic Fibrosis: A European Consensus, Eur. Respir. J., 2000 16:749–767.

Also suitable for combination with the compound of formula (I) are the antibiotic azithromycin and the antibiotic duramycin.

The compound of formula (I) can also be combined with antibacterial peptides derived from or related to the structure of defensins. Since secreted mucus presents a barrier which can prevent inhaled antibiotics or antibacterial peptides reaching target bacteria in the airways at sufficient concentration for effective antibacterial action, the prevention of mucin production by the compound of formula (I) is particularly useful as a means of enhancing the effectiveness of defensins, or antibiotics such as colistin, iseganan, or tobramycin, which are preferably administered by the inhaled route.

In view of the ability of the compound of formula (I) to block *Pseudomonas aeruginosa*-induced mucus production, a further particularly useful combination will be that of the compound of formula (I) with agents that enhance mucus clearance (B2), such as ambroxol. A detailed list of drugs which enhance mucus clearance is given by E. Houtmeyers et al., *Effects of Drugs on Mucus Clearance,* Eur. Respir. J., 1999, 14:452–467.

Another particularly useful combination is of the compound of formula (I) with drugs that reduce mucus production (B3) by other mechanisms than $LTB_4$ inhibition. Such drugs include but are not confined to drugs which inhibit the production or action of neutrophil elastase such as FK-706, CE 1037, EPI-HNE-4, and alpha 1-antitrypsin.

Drugs which reduce the amount of $LTB_4$ produced will reduce the amount of $LTB_4$ antagonist required to produce a therapeutic effect. Such drugs include but are not confined to $LTA_4$ hydrolase inhibitors such as those described in U.S. Pat. No. 5,723,492 and 5-lipoxygenase inhibitors such as atreleuton and zileuton. The combination of the compound of formula (I) and a compound from U.S. Pat. No. 5,723,492, or the compound of formula (I) and a 5-lipoxygenase inhibitor are particularly useful for the treatment of cystic fibrosis.

The weight ratio of the compound of formula (I) or salt thereof (A) to (B) may be, in general, from 100:1 to 1:200, for example from 75:1 to 1:190, from 75:1 to 1:150, from 60:1 to 1:120, from 50:1 to 1:100, from 50:1 to 1:50, from 30:1 to 1:40, form 20:1 to 1:20, from 10:1 to 1:15, from 8:1 to 1:10, from 4:1 to 1:10, or from 1:1 to 1:5. The two drugs (A) and (B) may be administered separately in the same ratio.

The compound of formula (I) may be administered orally, transdermally, by inhalation or parenterally. The compound of formula (I) occurs as active ingredients in conventional preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal systems etc. An effective dose of the compounds according to the invention is between 0.01 and 100, preferably between 0.1 and 50, most preferably between 5–30 mg/dose for oral administration, and between 0.001 and 50, preferably between 0.1 and 10 mg/dose for intravenous or intramuscular administration. For inhalation, according to the invention, solutions containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The administration of the compound of formula (I) once or twice a day for at least five days is preferred.

The compounds of formula (I) may be used on their own or in conjunction with other active substances according to the invention, optionally also in conjunction with other pharmacologically active substances. Suitable preparations include for example tablets, capsules, suppositories, solutions, elixirs, emulsions or dispersible powders.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, wetting agents, lubricants such as magnesium stearate or talc and/or agents for delaying release, such as carboxymethyl cellulose, cellulose acetate phthalate, polyvinylpyrrolidone or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g., with the addition of preservatives such as p-hydroxybenzoates, or stabilizers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 0.1 mg and 800 mg, preferably 10 mg to 500 mg, in particular 100 mg to 300 mg per adult.

It has now surprisingly been found that the potent, long acting $LTB_4$ antagonist of formula (I), is able to influence the *Pseudomonas aeruginosa*-induced transcription of a mucin gene.

The particular mucin gene here measured is muc-5AC RNA. This is the main mucin induced in rat epithelium by inflammatory stimuli. In man, studies with bronchial explants as well as isolated bronchial epithelial cells have shown that the transcription of this gene's human analogue, MUC-5AC, is upregulated by *Pseudomonas aeruginosa* (A. Dohrman, S. Miyata, M. Gallup et al., 1998, loc. cit.).

The $LTB_4$ antagonist of formula (I) has also surprisingly been found to be able to inhibit the increase in number of goblet cells in the tracheal epithelium following exposure to *Pseudomonas aeruginosa* toxin. Goblet cells are an important source of mucin. Goblet cells hyperplasia is a feature of cystic fibrosis (C. W. Bedrossian, S. D. Greenberg, D. B. Singer, J. J. Hansen, H. S. Rosenberg, *The Lung in Cystic Fibrosis: A Quantitative Study Including Prevalence of Pathologic Findings Among Different Age Groups,* Hum. Pathol., 1976, 7:195–204) and can also be induced experimentally in monkeys by exposure to *Pseudomonas aeruginosa* (A. T. Cheung, R. B. Moss, G. Kurland, A. B. Leong, W. J. Novick Jr., Chronic *Pseudomonas aeruginosa Endobronchitis in Rhesus Monkeys: II. A Histopathologic Analysis,* Med. Primatol., 1993, 22:257–262).

Biochemical Study of Effects of $LTB_4$ Antagonist (1) on Mucin RNA Production

Two different rat strains, BDE and F344/NHsd, were tested because previous studies had shown strain-related differences in reactivity to lipopolysaccharides.

| Materials and Methods Acronyms and Abbreviations | |
|---|---|
| CF | cystic fibrosis |
| FAM | 6-carboxyfluorescein |
| LPS | lipopolysaccharide |
| $LTB_4$ | leukotriene $B_4$, (5S,12R)-dihydroxy-6,14-cis-8,10-trans-eicosatetraenoic acid |
| PCR | polymerase chain reaction |
| TAMRA | 6-carboxytetramethylrhodamine |

Animals Used: Adult male rats, strain BDE/Han, average weight about 330 g (range 340 g to 450 g), and adult male F344/NHsd rats, average weight about 250 g (range 240 g to 260g).

Animal Maintenance: The rats were housed in air-conditioned rooms, at 21° C.–25° C., relative humidity between 50% and 65%, day-night cycle 12 hours. They were fed before the start of the experiment and received tap water ad lib. 18 hours prior to drug administration, food was withdrawn, but drinking water remained available.

The compound of formula (I), namely carbamic acid, [[4-[[3-[[4-[1-(4-hydroxyphenyl)-1-methylethyl]phenoxy]methyl]phenyl]methoxy]phenyl]iminomethyl]ethyl ester, was synthesized as described in the International Patent Application WO 96/02497 and jet milled. For administration to animals, the compound of formula (I) was first dissolved in LABRASOL® and a 7% emulsion was then prepared of this LABRASOL® solution in distilled water (homogenized). LABRASOL® is composed of a defined mixture of mono- di- and tri-glycerides and mono- and di-fatty acid esters of polyethylene glycol. Source: Gattefosse, 69804 Saint-Priest, France.

Lipopolysaccharide from *Pseudomonas aeruginosa* serotype 10, purified by gel filtration, lot 50K415 1. Purchased from Sigma, catalogue number L-8643.

Anesthetic: Isoflurane (FORENE®, Abbott).

Study Design

Exposure to Pseudomonas LPS: On the first day of the study the rats were primed by injection of 10 μg/kg/mL *Pseudomonas aeruginosa* lipopolysaccharide i.p. or saline vehicle. Food was then withdrawn. The following day the animals received the compound of formula (I) in 7% LABRASOL® or 7% LABRASOL® vehicle alone, and food was returned to the cages. 6 hours later the rats were exposed for 30 minutes in groups of six to an aerosol of *Pseudomonas aeruginosa* lipopolysaccharide. The aerosol was generated from a 100 μg/mL solution of *P. aeruginosa* LPS in isotonic saline using a DeVilbiss type 646 jet nebulizer driven by compressed air at 1.4 bar. The air was supplemented with 5% carbon dioxide to prevent breath-holding behavior by the rats. 20 hours after exposure the rats were killed by an overdose of FORENE®. A section of the trachea about 1 cm from the first bifurcation was removed, shock-frozen in liquid nitrogen and stored at −80° C.

Extraction and Quantitation of RNA: Total RNA was isolated with the RNeasy system (Qiagen, Germany). The kit method was slightly modified by inclusion of an extra digestion step with RNAase-free DNAase (Qiagen, Catalogue No. 79254, incubation 30 minutes at room temperature). Quality of the extracted RNA was checked by agarose gel electrophoresis. Quantitation of muc-5AC RNA was performed by the TAQMAN® real time PCR system using an ABI Prism 7700 Detector (Perkin Elmer Corporation, California USA). Probes were designed on the basis of gene bank sequence GI "2315984". The forward probe was 5'-TGG GAA CCA TCA TCT ACA ACC A-3', the reverse probe 5'-TCC TGA CTA ACC CCT TTG ACC A-3' and the fluorogenic probe 5'-CCT TGA CGG CCA CTG TTA CTA TGC GAT GT-3', labeled with the fluor FAM at the 5'-end and the quencher TAMRA at the 3'-end. Ribosomal RNA was used as the housekeeping gene to which all muc-5AC RNA measurements were compared (Taqman ribosomal RNA control reagents (VIC™ Probe), Applied Biosystems). The master mix was the standard TAQMAN® EZ RT-PCR core mix sold by Applied Biosystems (Catalogue No. N808-0236). For muc-5AC assay it was supplemented with 2 mM manganese and the forward and reverse primers were both used at concentration 300 nM. The temperature sequence (auto ramp) was as follows: 50° C., 10 minutes (reverse transcription); 60° C., 30 minutes (DNA polymerase); 95° C., 5 minutes (separation of double strand into two single strands); and 40 cycles of 20 seconds at 94° C. and 1 minute at 59° C. (polymerase chain reaction). For the ribosomal RNA assay the annealing temperature was 60° C. instead of 59° C. On each plate, each sample was measured in duplicate, first with the ribosomal RNA then the muc-5 AC RNA. For each sample and pair of plates a ratio of muc-5AC RNA to ribosomal RNA was calculated. The plates were then repeated for all samples, and the mean muc-5AC RNA to ribosomal RNA calculated from the measurements on the two sets of plates. For standardization purposes, one sample (from an RNA pool derived from rat tracheas exposed to *E. coli* O55.B5 lipopolysaccharide) was measured on both of the duplicate plates.

Statistical Analysis

For each rat strain the positive control were compared with the negative control and the group treated with the compound of formula (I) by one sided Wilcoxon tests. Because of the multiple test situation the p values were adjusted according to Bonferroni-Holm for each experiment to control the level of significance ($\alpha=0.05$) (9). Furthermore the two rat strains were compared for each group with a two sided Wilcoxon test ($\alpha=0.05$). The statistical analysis was carried out with the program SAS (SAS Institute Inc., Cary, N.C.), version 6.12.

Results

Exposure of rats of either the BDE strain or F344 strain to *Pseudomonas aeruginosa* aerosol caused a marked increase in the tracheal epithelial expression (relative to a 18S ribosomal RNA housekeeping gene) of the muc-5AC gene (p=0.004). In the BDE rats the increase in muc-5AC expression after Pseudomonas exposure was more than 27 fold, in the F344 rats (largely because of higher control values for muc-5AC expression in the untreated animals) more than 10 fold. Prior treatment with the $LTB_4$ antagonist of formula (I) at 3 mg/kg p.o. reduced this increase to less than half the value with only vehicle pre-treatment. This effect of the compound of formula (I) was statistically significant whether the BDE strain was studied (when p=0.003) or the F344 strain was studied (p=0.010).

Histological Study of Effects of $LTB_4$ Antagonist (I) on Mucin-Containing Goblet Cells This study was only carried out in BDE strain rats, these having given good results in the previous biochemical study.

Materials and Methods

Animals Used: Adult male rats, strain BDE/Han, with approximately the same average weight as in the biochemical study (described above).

Animal Maintenance: The rats were housed as in the previous study. As the duration of histological study was considerably greater than that of the biochemical study, the rats were not fasted.

The compound of formula (I) was synthesized and formulated for administration to the rats as in the previous study.

Lipopolysaccharide from *Pseudomonas aeruginosa* serotype 10, as in the previous study.

Anesthetic: Isoflurane (FORENE®, Abbott).

Study Design

Exposure to Pseudomonas LPS and Section Preparation: The technique for priming the rats and aerosol exposure to *Pseudomonas aeruginosa* lipopolysaccharide was as described earlier. However, in the histological study the rats were killed 96 hours after exposure to the *Pseudomonas aeruginosa* lipopolysaccharide aerosol. The longer period between exposing the mice to Pseudomonas aerosol and killing them was necessary because histological changes occur more slowly than changes in mRNA expression. Animals were given the compound (I) in 7% LABRASOL® per os 5 hours before and 21, 45, 69, and 93 hours after the *Pseudomonas aeruginosa* aerosol. At sacrifice, 3 hours after the last treatment with compound (I), the complete lung was removed, fixed in 7% buffered formalin and embedded in paraffin. The left main stem bronchus was used for immunohistochemical staining. Lung sections were cut to include the full length of the main intrapulmonary airway and stained sequentially with hematoxylin and eosin or with Alcian blue (AB)-periodic acid-Schiff (PAS) to evaluate the total epithelial area and the area stained for intracellular mucous glycoconjugates, respectively. Goblet cell production was determined by the volume density of AB-PAS-stained mucous glycoconjugates on the epithelial mucosal surface using an image analysis system (Soft Imaging System, Münster, Germany). The number of AB-PAS staining goblet cells and the total epithelial area were measured over a length of 2 mm of the basal lamina.

Results

Exposure of rats to *Pseudomonas aeruginosa* lipopolysaccharide caused a marked increase in the number of goblet cells per square millimeter epithelium. Treatment with 3 mg/kg p.o. compound (I) reduced the effect of Pseudomonas aerosol treatment (see table below). The mean number of goblets cells per square millimeter was 507 in the negative control, 1669 in the *Pseudomonas aeruginosa* treated positive control, and 408 in the group treated with both *Pseudomonas aeruginosa* aerosol and compound (I) 3 mg/kg per os.

| Treatment | Number of Goblet Cells/Square Millimeter Epithelium |
|---|---|
|  | 137 |
|  | 66 |
|  | 1882 |
| Negative Control | 1183 |
| (saline aerosol) | 246 |
|  | 320 |
|  | 70 |
|  | 150 |
|  | 1928 |
|  | 1605 |
|  | 1641 |
| Positive Control | 713 |
| (*P. aeruginosa* aerosol) | 2553 |
|  | 1375 |
|  | 2301 |
|  | 1238 |
|  | 906 |
|  | 215 |
| *P. aeruginosa* aerosol | 519 |
| plus 3 mg/kg p.o. | 175 |
| compound (I) administered | 306 |
| 5 hours prior to the aerosol | 530 |
| and daily thereafter | 249 |
|  | 362 |

What is claimed is:

1. A method of treating or preventing goblet cell hyperplasia induced by products of pathogenic bacteria in a patient in need of such treatment, the method comprising administering to the patient a therapeutically effective amount of an LTB$_4$ antagonist of formula (I)

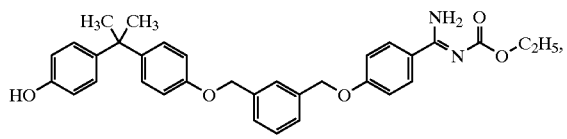

(I)

a tautomer thereof or a pharmaceutically acceptable salt thereof.

2. A method of treating or preventing diseases caused by increased expression of mucin genes in the bronchial or gastrointestinal epithelium in a patient in need of such treatment, wherein the increased expression of mucin genes is effected by *Pseudomonas aeruginosa* or products derived therefrom, the method comprising administering to the patient a therapeutically effective amount of an LTB$_4$ antagonist of formula (I)

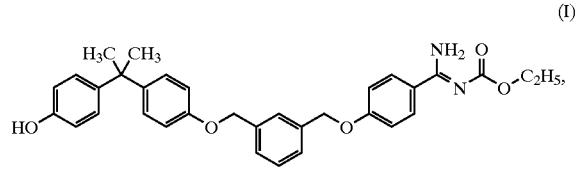

(I)

a tautomer thereof or a pharmaceutically acceptable salt thereof.

3. The method according to claim 1, wherein the goblet cell hyperplasia is effected by *Pseudomonas aeruginosa* or products derived therefrom.

4. A method of inhibiting the increase in number of goblet cells in the tracheal epithelium following exposure to *Pseudomonas aeruginosa* toxin in a patient in need of such treatment, the method comprising administering to the patient a therapeutically effective amount of an LTB$_4$ antagonist of formula (I)

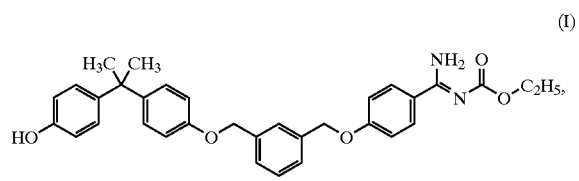

(I)

a tautomer thereof or a pharmaceutically acceptable salt thereof.

5. The method according to one of claims 1 to 4, wherein the therapeutically effective amount of an LTB$_4$ antagonist of formula (I) is between 5 mg to 200 mg.

6. The method according to one of claims 1 to 4, wherein an additional active ingredient selected from the group consisting of antibiotics, LTA$_4$ hydrolase inhibitors, 5-lipoxygenase inhibitors, and agents that enhance mucus clearance, are administered simultaneously or sequentially with the LTB$_4$ antagonist of formula (I).

7. The method according to one of claims 1 to 4, wherein an additional active ingredient selected from the group consisting of aminoglycoside antiboitics, antibacterial peptides derived from or related to the structure of defensins, and agents which inhibit the production or action of neutrophil elastase, are administered simultaneously or sequentially with LTB$_4$ antagonist of formula (I).

8. The method according to one of claims 1 to 4, wherein an additional active ingredient selected from the group consisting of atreleuton, zileuton, FK-706, CE 1037, EPI-HNE-4, alpha 1-antitrypsin, ambroxol, gentamycin, amikacin, kanamycin, streptomycin, neomycin, netimicin, colistin, iseganan, and tobramycinare, administered simultaneously or sequentially with the LTB$_4$ antagonist of formula (I).

* * * * *